(12) United States Patent
Yang et al.

(10) Patent No.: US 12,303,534 B2
(45) Date of Patent: May 20, 2025

(54) PHARMACEUTICAL COMPOSITION COMPRISING MESENCHYMAL STEM CELLS AS EFFECTIVE INGREDIENT FOR PREVENTION OR TREATMENT OF INFLAMMATORY DISEASE

(71) Applicant: MEDIPOST CO., LTD., Seongnam-si (KR)

(72) Inventors: Yun Sun Yang, Seongnam-si (KR); Wonil Oh, Seongnam-si (KR); Soo Jin Choi, Seongnam-si (KR); Jihye Kwak, Seongnam-si (KR); Dong Hyon Kim, Seongnam-si (KR); Hoon Lim, Seongnam-si (KR)

(73) Assignee: MEDIPOST CO., LTD, Seongnam-si (KR)

( * ) Notice: Subject to any disclaimer, the term of this patent is extended or adjusted under 35 U.S.C. 154(b) by 772 days.

(21) Appl. No.: 16/972,118

(22) PCT Filed: Jun. 5, 2019

(86) PCT No.: PCT/KR2019/006817
§ 371 (c)(1),
(2) Date: Dec. 4, 2020

(87) PCT Pub. No.: WO2019/235854
PCT Pub. Date: Dec. 12, 2019

(65) Prior Publication Data
US 2021/0228636 A1    Jul. 29, 2021

Related U.S. Application Data

(60) Provisional application No. 62/680,748, filed on Jun. 5, 2018.

(51) Int. Cl.
| | | |
|---|---|---|
| A61K 35/28 | (2015.01) | |
| A61K 9/00 | (2006.01) | |
| A61K 31/728 | (2006.01) | |
| A61K 35/51 | (2015.01) | |
| A61P 11/06 | (2006.01) | |
| A61P 19/02 | (2006.01) | |
| A61P 25/28 | (2006.01) | |

(52) U.S. Cl.
CPC ............ *A61K 35/28* (2013.01); *A61K 9/0019* (2013.01); *A61K 31/728* (2013.01); *A61K 35/51* (2013.01); *A61P 11/06* (2018.01); *A61P 19/02* (2018.01); *A61P 25/28* (2018.01)

(58) Field of Classification Search
CPC .................................. A61K 35/51; A61P 25/28
See application file for complete search history.

(56) References Cited

U.S. PATENT DOCUMENTS

2017/0166869 A1   6/2017   Gonzalez
2018/0110807 A1   4/2018   Ilagan et al.

FOREIGN PATENT DOCUMENTS

| JP | 2018-513388 A | 5/2018 |
| KR | 10-2015-0039214 A | 4/2015 |
| WO | 2016/170187 A2 | 10/2016 |
| WO | 2018/083700 A1 | 5/2018 |

OTHER PUBLICATIONS

Zarrabi (2014, Cell Journal, vol. 15, pp. 274-281).*
Kwak, Bioengineering 2022, 9, 177. https://doi.org/10.3390/bioengineering9040177, 16 pages.*
Xia, 2020, Leukemia, 34:2375-2383.*
Lu (Biomedicine and Pharmacotherapy, 165:9 pages).*
Kim, 2013, Gastroenterology; 145:1392-1403.*
Lee, Neurobiology of Aging, 33 (2012) 588-602.*
Damien, Biol Blood Marrow Transplant 21 (2015) 1545-1554.*
Adiba Isa et al., "Impaired Cell Surface Expression of HLA-B Antigens on Mesenchymal Stem Cells and Muscle Cell Progenitors", PloS one, May 2010, pp. 1-11, vol. 5, No. 5, e10900.
International Searching Authority, International Search Report of PCT/KR2019/006817 dated Sep. 11, 2019 [PCT/ISA/210].
Fabio Morandi et al., "Immunogenicity of Human Mesenchymal Stem Cells in HLA-Class I-Restricted T-Cell Responses Against Viral or Tumor-Associated Antigens", Stems Cells, 2008, vol. 26, pp. 1275-1287 (13 pages).

* cited by examiner

*Primary Examiner* — Valarie E Bertoglio
(74) *Attorney, Agent, or Firm* — Sughrue Mion, PLLC

(57) ABSTRACT

A pharmaceutical composition comprising HLA-A2-expressing mesenchymal stem cells as an effective ingredient and its use in prevention or treatment of inflammatory disease are disclosed. The mesenchymal stem cells expressing HLA-A2 on the surface thereof inhibit the secretion of the inflammatory cytokine TNF-a and increase the expression of the anti-inflammatory markers CD163 and Arg-1, so that the pharmaceutical composition comprising the mesenchymal stem cells as an effective ingredient can be advantageously used for suppressing inflammation or treating inflammatory diseases.

8 Claims, 11 Drawing Sheets
Specification includes a Sequence Listing.

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: HLA-A2 siRNA (sense)

<400> SEQUENCE: 1
```

-continued

```
guucguguag gcauaaugut t                                          21

<210> SEQ ID NO 2
<211> LENGTH: 21
<212> TYPE: DNA
<213> ORGANISM: Artificial Sequence
<220> FEATURE:
<223> OTHER INFORMATION: HLA-A2 siRNA (anti-sense)

<400> SEQUENCE: 2
acauuaugcc uacacgaact t                                          21

<210> SEQ ID NO 3
<211> LENGTH: 21
<212> TYPE: DNA
<213> ORGANISM: Artificial Sequence
<220> FEATURE:
<223> OTHER INFORMATION: control siRNA (sense)

<400> SEQUENCE: 3
ccuacgccac caauuucgut t                                          21

<210> SEQ ID NO 4
<211> LENGTH: 21
<212> TYPE: DNA
<213> ORGANISM: Artificial Sequence
<220> FEATURE:
<223> OTHER INFORMATION: control siRNA (anti-sense)

<400> SEQUENCE: 4
acgaaauugg uggcguaggt t                                          21
```

PHARMACEUTICAL COMPOSITION COMPRISING MESENCHYMAL STEM CELLS AS EFFECTIVE INGREDIENT FOR PREVENTION OR TREATMENT OF INFLAMMATORY DISEASE

CROSS REFERENCE TO RELATED APPLICATIONS

This application is a National State Application of PCT/KR2019/006817 filed Jun. 5, 2019, which claims benefit of Provisional Application No. 62/680,748 filed Jun. 5, 2018.

TECHNICAL FIELD

The present invention relates to a pharmaceutical composition for preventing or treating an inflammatory disease, comprising, as an active ingredient, mesenchymal stem cells expressing HLA-A2 and its use in preventing or treating an inflammatory disease.

BACKGROUND ART

Inflammation is usually a localized protective response elicited by foreign substances or harmful stimuli. Direct causes of inflammation include infectious agents such as bacteria, viruses, and parasites; physical factors such as burns or irradiation; chemicals such as toxins and drugs; immunological responses such as allergies and autoimmune responses, and the like.

In general, antibiotics are used for inflammation caused by bacterial infection, and anti-inflammatory enzymes are used for painless inflammation with pus or the like. In addition, nonsteroidal anti-inflammatory drugs are used for inflammation with severe pain, and immunosuppressants or steroids are used for inflammation caused by abnormal immune system. However, the immunosuppressants and steroids are problematic in that the immunosuppressants are directly involved in the immune system and thus have a high incidence of adverse effects; and the steroids also exhibit adverse effects in a case of being used for a long period of time and discontinuation of the same leads to relapse of disease symptoms.

Recently, to overcome these adverse effects, treatments using stem cells are under the spotlight in the biopharmaceutical market. Among the stem cells, mesenchymal stem cells (MSCs) can differentiate into several cell lineages such as adipocytes, osteocytes, and chondrocytes. In addition, the mesenchymal stem cells have an advantage of being able to be isolated from many tissues such as compact bone, peripheral blood, adipose tissue, umbilical cord blood, and amniotic membrane, in addition to bone marrow.

DISCLOSURE OF INVENTION

Technical Problem

The present inventors have identified that mesenchymal stem cells expressing HLA-A2 exhibit a superior anti-inflammatory effect in vitro to mesenchymal stem cells not expressing HLA-A2. In addition, the present inventors have also identified that the mesenchymal stem cells expressing HLA-A2 exhibit an excellent anti-inflammatory effect in a bronchopulmonary dysplasia-induced mouse model and an Alzheimer's disease-induced mouse model.

Solution to Problem

In an aspect of the present invention, there is provided a pharmaceutical composition for preventing or treating an inflammatory disease, comprising, as an active ingredient, mesenchymal stem cells expressing HLA-A2 on a surface thereof.

In another aspect of the present invention, there is provided a method for preventing or treating an inflammatory disease, comprising a step of administering the pharmaceutical composition to an individual.

In yet another aspect of the present invention, there is provided a use of mesenchymal stem cells expressing HLA-A2 on a surface thereof for manufacture of a medicament for preventing or treating an inflammatory disease.

In still yet another aspect of the present invention, there is provided a method for selecting mesenchymal stem cells having excellent inflammation inhibition ability, comprising a step of isolating mesenchymal stem cells expressing HLA-A2 on a surface thereof.

Advantageous Effects of Invention

The mesenchymal stem cells expressing HLA-A2 on a surface thereof according to the present invention inhibit secretion of TNF-α, which is an inflammatory cytokine, and increase expression of CD163 and Arg-1, which are anti-inflammatory markers, so that a pharmaceutical composition which comprises the mesenchymal stem cells as an active ingredient can be effectively used to inhibit inflammation or treat an inflammatory disease.

DETAILED DESCRIPTION OF INVENTION

Figure 1:
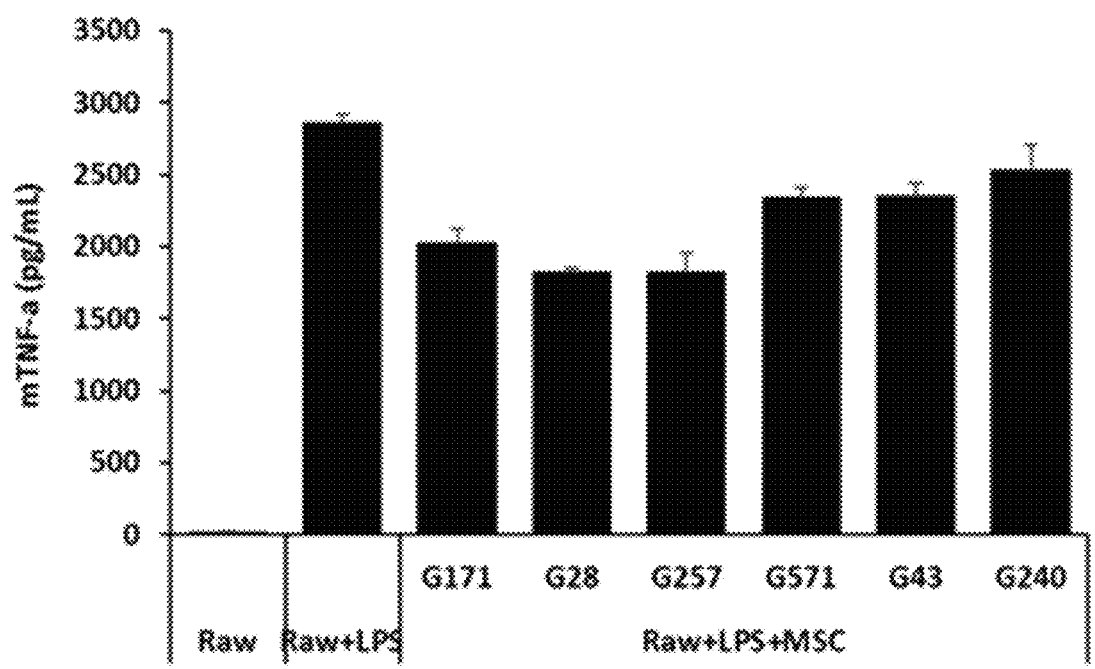
FIG. 1 illustrates results obtained by subjecting Raw264.7 cells, which have been treated with LPS to induce an inflammatory response, to treatment with mesenchymal stem cells expressing HLA-A2 (Lots: G171, G28, and G257) or mesenchymal stem cells not expressing HLA-A2 (Lots: G571, G43, and G240), and then measuring an amount of mTNF-α secreted.

Hereinafter, the present invention will be described in detail.

In an aspect of the present invention, there is provided a composition for preventing or treating an inflammatory disease, comprising, as an active ingredient, mesenchymal stem cells expressing human leukocyte antigen A2 (HLA-A2) on a surface thereof.

The HLA-A2 is a human leukocyte antigen (HLA) serotype within the HLA-A serotype group, in which the HLA is a glycoprotein molecule encoded by the major histocompatibility complex (MHC) gene complex in humans. The HLA-A is expressed on a surface of all nucleated cells and platelets, and plays a role in antigen recognition when cytotoxic T cells recognize and eliminate virus-infected cells or tumor cells. So far, no reports have been made about an inflammation inhibitory effect of human-derived mesenchymal stem cells expressing HLA-A2.

The present invention is based on the results that mesenchymal stem cells expressing HLA-A2 on a surface thereof have superior inflammation inhibition ability to mesenchymal stem cells not expressing HLA-A2. Specifically, in an embodiment of the present invention, the mesenchymal stem cells expressing HLA-A2 on a surface thereof of the present invention are characterized in that these cells express HLA-A2 at a level that is higher than mesenchymal stem cells not expressing HLA-A2 by 70%, 75%, 80%, 85%, 90% or 95%, or higher.

In addition, on a surface thereof, the mesenchymal stem cells of the present invention may express any one selected from the group consisting of cluster of differentiation 73 (CD73), CD90, CD105, CD166, and combinations thereof, and may not express any one selected from the group consisting of CD14, CD34, CD45, human leukocyte antigen DR (HLA-DR), and combinations thereof.

Specifically, on a surface thereof, the mesenchymal stem cells of the present invention may express each of CD73, CD90, CD105, and CD166 at a level of 70% or higher, and may express each of CD14, CD34, CD45, and HLA-DR at a level of 1% or lower. More specifically, on a surface thereof, the mesenchymal stem cells of the present invention may express HLA-A2 at a level of 75% or higher, may express each of CD73, CD90, CD105, and CD166 at a level of 70% or higher, and may express each of CD14, CD34, CD45, and HLA-DR at a level of 1% or lower.

The CD73 is also called 5'-nucleotidase (5'-NT) and is an enzyme encoded by the NT5E gene. The CD73 functions to convert adenosine monophosphate (AMP) to adenosine.

The CD90 is a cell surface protein composed of N-glycosylated glycophosphatidylinositol (GPI) and a single V-like immunoglobulin domain.

The CD105, which is also called endoglin (ENG), is a type I membrane glycoprotein located on a cell surface and is part of the TGF beta receptor complex.

The CD166 is a type I transmembrane glycoprotein that is located on a cell surface and a member of the immunoglobulin superfamily of proteins. The CD166 is encoded by the ALCAM gene.

The CD14 is a pattern recognition receptor (PRR) and is one of the components of the innate immune system. For detection of bacterial lipopolysaccharide (LPS), the CD14 acts together with the co-receptors, toll-like receptor 4 (TLR 4) and MD-2, to bind to LPS in the presence of lipopolysaccharide-binding protein (LBP).

The CD34 is a transmembrane phosphoglycoprotein encoded by the CD34 gene in humans.

The CD45 is a protein tyrosine phosphatase (PTP) enzyme encoded by the PTPRC gene in humans.

The HLA-DR is a cell surface receptor that belongs to Class II of HLA, and is involved in autoimmunity, disease susceptibility, disease resistance, and the like.

As the mesenchymal stem cells, any mesenchymal stem cells may be used regardless of their origin, and umbilical cord blood-derived mesenchymal stem cells may be preferably used.

In addition, a content of mesenchymal stem cells expressing HLA-A2 in the pharmaceutical composition may be $1.0 \times 10^5$ cells/ml to $1.0 \times 10^8$ cells/ml, and may be specifically $1.0 \times 10^5$ cells/ml to $1.0 \times 10^8$ cells/ml or $2.0 \times 10^5$ cells/ml to $5.0 \times 10^7$ cells/ml. Preferably, the content of mesenchymal stem cells expressing HLA-A2 in the pharmaceutical composition may be $5.0 \times 10^6$ cells/ml to $3 \times 10^7$ cells/ml. In an embodiment of the present invention, 50 µl of a solution having a content of $1 \times 10^7$ cells/ml was administered to mice.

The pharmaceutical composition is a cell therapeutic agent and may further comprise a pharmaceutically acceptable carrier. The carrier is commonly used in manufacture of drugs, and examples thereof include lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, mineral oil, and the like.

In addition, the pharmaceutical composition of the present invention may further comprise a pharmaceutically acceptable additive selected from the group consisting of lubricants, wetting agents, sweetening agents, flavoring agents, emulsifying agents, suspending agents, preservatives, and combinations thereof.

With respect to a total weight of the pharmaceutical composition of the present invention, the carrier may be contained in an amount of about 1% to about 99.99% by weight and preferably about 90% to about 99.99% by weight, and the pharmaceutically acceptable additive may be contained in an amount of about 0.1% to about 20% by weight.

The pharmaceutical composition may be prepared in a unit dosage form by being formulated with pharmaceutically acceptable carriers and excipients according to a conventional method, or the formulations may be placed in a multi-dose container. Here, the formulation may be in the form of a solution, a suspension, a syrup, or an emulsion in oil or aqueous media, or in the form of an extract, powders, granules, or capsules; and may further comprise a dispersing or stabilizing agent.

The inflammatory disease refers to a disease accompanied by inflammation. The inflammatory disease may include, but is not limited to, rheumatoid arthritis, atopy, asthma, allergic rhinitis, Alzheimer's disease, graft versus host disease (GVHD), diabetic nephropathy, Crohn's disease, inflammatory bowel disease, rejection after transplantation, bronchopulmonary dysplasia (BPD), or chronic obstructive pulmonary disease (COPD).

In another aspect of the present invention, there is provided a method for preventing or treating an inflammatory disease, comprising a step of administering, to an individual, a pharmaceutical composition for treating an inflammatory disease which comprises mesenchymal stem cells expressing HLA-A2 on a surface thereof.

The mesenchymal stem cells expressing HLA-A2 are the same as those as described above in the pharmaceutical composition.

The individual may be a mammal, specifically a human. Regarding administration route and dose of the pharmaceutical composition, the pharmaceutical composition may be administered to a subject in various methods and amounts depending on the subject's condition and the presence or absence of adverse effects; and the optimal administration method and dose may be selected in an appropriate range by a person skilled in the art. In addition, the pharmaceutical composition may be administered in combination with other drugs or physiologically active substances which are known to have a therapeutic effect on an inflammatory disease to be treated, or may be formulated in the form of a combination formulation with other drugs.

In a case where the pharmaceutical composition is administered parenterally, the pharmaceutical composition may be administered, for example, via subcutaneous, ocular, intraperitoneal, intramuscular, oral, rectal, intraorbital, intracerebral, intracranial, intraspinal, intraventricular, intrathecal, intranasal, or intravenous route.

The administration may be made once or more, or 1 to 3 times, with 3 times being specifically mentioned. In a case of repeated administration, the administration may be made at intervals of 1 to 56 days, 7 to 49 days, 14 to 42 days, or 21 to 35 days. Preferably, the administration may be made at intervals of 28 days. In a case where a large dose is administrated, the administration may be made several times a day.

A dose of the mesenchymal stem cells expressing HLA-A2 may be $1\times10^6$ cells/individual to $1\times10^8$ cells/individual. Specifically, the dose of the mesenchymal stem cells expressing HLA-A2 may be $5\times10^4$ cells/kg to $1\times10^7$ cells/kg, $1\times10^5$ cells/kg to $7\times10^6$ cells/kg, or $2\times10^5$ cells/kg to $5\times10^5$ cells/kg.

In yet another aspect of the present invention, there is provided a use of mesenchymal stem cells expressing HLA-A2 on a surface thereof for manufacture of a medicament for preventing or treating an inflammatory disease.

In still yet another aspect of the present invention, there is provided a method for selecting mesenchymal stem cells having excellent inflammation inhibition ability, comprising a step of isolating mesenchymal stem cells expressing HLA-A2 on a surface thereof.

Regarding the selection method, a method of isolating mesenchymal stem cells expressing HLA-A2 on a surface thereof may be performed using, for example, a flow cytometer.

In an embodiment of the present invention, mesenchymal stem cells were treated with anti-CD14 antibody, anti-CD34 antibody, anti-CD45 antibody, anti-HLA-DR antibody, anti-CD73 antibody, anti-CD90 antibody, anti-CD105 antibody, anti-CD166 antibody, and mouse anti-HLA-A2 antibody, to analyze their cell surface antigens. Then, only the mesenchymal stem cells expressing HLA-A2, CD73, CD90, CD105, and CD166 were given electric charges and passed through an electric field. In this manner, the mesenchymal stem cells expressing HLA-A2 on a surface thereof were isolated.

MODE FOR THE INVENTION

Hereinafter, the present invention will be described in more detail by way of the following examples. However, the following examples are for illustrative purposes only, and the scope of the present invention is not limited thereto.

Example 1: Identification of Umbilical Cord Blood-Derived Mesenchymal Stem Cells Expressing HLA-A2 on Surface Thereof For the umbilical cord blood-derived mesenchymal stem cells, mesenchymal stem cells were first isolated from umbilical cord blood, and then were passaged 5 times. The passaged mesenchymal stem cells (at 5 passage) were cryopreserved in liquid nitrogen so as to be used in several lots. The cryopreserved mesenchymal stem cells were thawed for about 3 minutes in a constant temperature water bath at 37° C. Then, the mesenchymal stem cells were resuspended in α-MEM medium containing 10% (v/v) fetal bovine serum (FBS), and centrifuged with a centrifuge at 1,200 rpm for 5 minutes. After completion of the centrifugation, the supernatant was removed and the remaining mesenchymal stem cells were resuspended in phosphate buffer saline (PBS).

Thereafter, to analyze cell surface antigens of the umbilical cord blood-derived mesenchymal stem cells, the cells were allowed to react for 15 minutes, in the dark at 25° C., with anti-CD14 antibody (BD Pharmigen, Cat #555397), anti-CD34 antibody (BD Pharmigen, Cat #555822), anti-CD45 antibody (BD Pharmigen, Cat #555482), anti-HLA-DR antibody (BD Pharmigen, Cat #555811), anti-CD73 antibody (BD Pharmigen, Cat #550257), anti-CD90 antibody (Invitrogen, Cat #12-0909-42), anti-CD105 antibody (Invitrogen, Cat #12-1057-42), anti-CD166 antibody (BD Pharmigen, Cat #555263), and mouse anti-HLA-A2 antibody (BD Pharmigen, Cat #558570). After completion of the reaction, washing was performed once with PBS and centrifugation was performed at 1,200 rpm for 5 minutes, to isolate only the mesenchymal stem cells. Each tube was treated with 200 μl of formaldehyde at a concentration of 1% so that the cells were fixed. Here, analysis of the cell surface antigens was performed using the MACSQUANT® Analyzer 10 flow cytometer (Miltenyi biotec, Bergisch Gladbach, Germany) and the MACS Quantify software. The analysis results are shown in Table 1 below.

TABLE 1

| Lot | | HLA-A2 (+) | | | HLA-A2 (−) | |
|---|---|---|---|---|---|---|
| No. | 10G171 | 09G028 | 11G257 | 12G571 | 08G043 | 11G240 |
| negative markers CD14 | 0.54% | 0.47% | 0.19% | 0.60% | 0.59% | 0.53% |
| CD34 | 0.47% | 0.33% | 0.46% | 0.81% | 1.44% | 0.61% |
| CD45 | 0.46% | 0.44% | 0.20% | 0.68% | 0.62% | 0.42% |
| HLA-DR | 0.80% | 0.42% | 0.39% | 0.65% | 1.28% | 0.34% |
| positive markers CD73 | 84.60% | 93.30% | 99.56% | 77.59% | 96.91% | 93.91% |
| CD90 | 71.54% | 76.66% | 99.71% | 67.42% | 90.87% | 86.44% |
| CD105 | 80.40% | 94.36% | 99.34% | 58.54% | 97.05% | 99.59% |
| CD166 | 78.86% | 91.10% | 99.51% | 51.90% | 98.19% | 99.26% |
| HLA-A2 | 77.59% | 85.23% | 99.20% | 0.63% | 0.87% | 0.49% |

As shown in Table 1, it was identified that on a surface thereof, the umbilical cord blood-derived mesenchymal stem cells in Lots G171, G028, and G257 expressed HLA-A2 at a level of 70% or higher. On the other hand, it was identified that on a surface thereof, the umbilical cord blood-derived mesenchymal stem cells in Lots G571, G043, and G240 expressed HLA-A2 at a level of lower than 1%. From the above analysis, a group (HLA-A2(+)) of mesenchymal stem cells expressing HLA-A2 on a surface thereof and a group (HLA-A2(−)) of mesenchymal stem cells not expressing HLA-A2 on a surface thereof were clearly distinguished from each other.

Example 2: Identification of Inflammation Inhibitory Effect of Umbilical Cord Blood-Derived Mesenchymal Stem Cells Expressing HLA-A2 (I)

To compare inflammation inhibitory efficacy of the mesenchymal stem cells depending on their HLA-A2 expression, an inflammation inhibitory effect of the mesenchymal stem cells in each lot was checked.

Specifically, Raw 264.7 cells, which are mouse-derived macrophages, were treated with lipopolysaccharide (LPS), an inflammatory stimulating substance, so that an inflammatory response was induced. The mesenchymal stem cells in each lot, which had been cryopreserved, were thawed for about 3 minutes in a constant temperature water bath at 37° C. Then, the mesenchymal stem cells were resuspended in α-MEM medium containing 10% (v/v) fetal bovine serum (FBS), and centrifuged with a centrifuge at 1,200 rpm for 5 minutes. After completion of the centrifugation, the supernatant was removed and the remaining mesenchymal stem cells were resuspended in RPMI medium.

Using RPMI medium containing 1 g/ml of LPS, $2\times10^4$ Raw264.7 cells were co-incubated with $2\times10^4$ mesenchymal stem cells in Lot G171, G028, G257, G571, G043, or G240 in each well. After 24 hours, the culture medium was collected and an amount of mTNF-α secreted was analyzed using the QUANTIKINE® mouse TNF-α Immunoassay kit (R&D Systems).

As a result, as illustrated in FIG. 1, it was identified that an amount of mTNF-α secreted was further decreased in the Raw264.7 cells in a case where the Raw264.7 cells were co-incubated with the mesenchymal stem cells in Lot G171, G028, or G257 as compared with a case where the Raw264.7 cells were co-incubated with the mesenchymal stem cells in Lot G571, G043, or G240.

Figure 2:
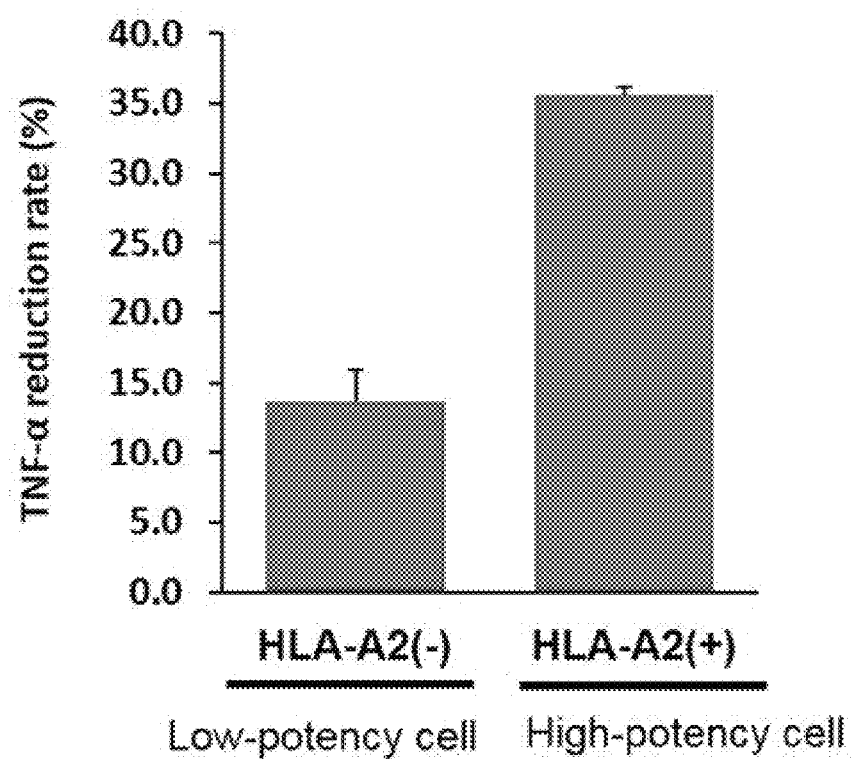
FIG. 2 illustrates results obtained by subjecting Raw264.7 cells, which have been treated with LPS to induce an inflammatory response, to treatment with mesenchymal stem cells expressing HLA-A2 (Lots: G171, G28, and G257) or mesenchymal stem cells not expressing HLA-A2 (Lots: G571, G43, and G240), and then calculating an mTNF-α secretion reduction rate.

In addition, based on the amount of mTNF-α secreted as measured above, a reduction rate thereof was calculated. As a result, it was identified that the group of mesenchymal stem cells (HLA-A2(+): G171, G028, G257) expressing HLA-A2 on a surface thereof exhibited an mTNF-α secretion reduction rate of about 35%, whereas the group of mesenchymal stem cells (HLA-A2(−): G571, G043, G240) not expressing HLA-A2 on a surface thereof exhibited an mTNF-α secretion reduction rate of 15% or lower (FIG. 2).

Example 3: Identification of Inflammation Inhibitory Effect of Umbilical Cord Blood-Derived Mesenchymal Stem Cells Expressing HLA-A2 on Surface Thereof (II)

To identify whether in a case where inhibition of expression of HLA-A2 in mesenchymal stem cells also results in inhibition of an anti-inflammatory effect of the mesenchymal stem cells, siRNA was used to inhibit expression of HLA-A2 in the mesenchymal stem cells for comparison of an inflammation inhibitory effect.

Raw 264.7 cells, which are mouse-derived macrophages, were treated with lipopolysaccharide (LPS), an inflammatory stimulating substance, so that an inflammatory response was induced. Then, the mesenchymal stem cells expressing HLA-A2 (HLA-A2(+)-MSC) were treated with control siRNA (SEQ ID NOS: 3 and 4) (HLA-A2(+)-MSC-siCON) or siRNA against HLA-A2 (SEQ ID NOS: 1 and 2) (HLA-A2(+)-MSC-siHLA-A2), and then co-incubated with the inflammatory response-induced Raw 264.7 cells. Subsequently, an amount of mTNF-α secreted was checked in the respective Raw 264.7cells.

Specifically, the mesenchymal stem cells in Lot G027, G074, G171, G610, G028, or G257 were prepared by treatment with the control siRNA (HLA-A2(+)-MSC-siCON) or the SiRNA against HLA-A2 (HLA-A2(+)-MSC-siHLA-A2).

Then, using RPMI medium containing LPS at a concentration of 1 g/ml, $2\times10^4$ Raw264.7 cells were co-incubated with $2\times10^4$ prepared mesenchymal stem cells in each well. After 24 hours, the culture medium was collected and an amount of mTNF-α secreted was analyzed using the QUANTIKINe® mouse TNF-α Immunoassay kit (R&D Systems).

Figure 3:
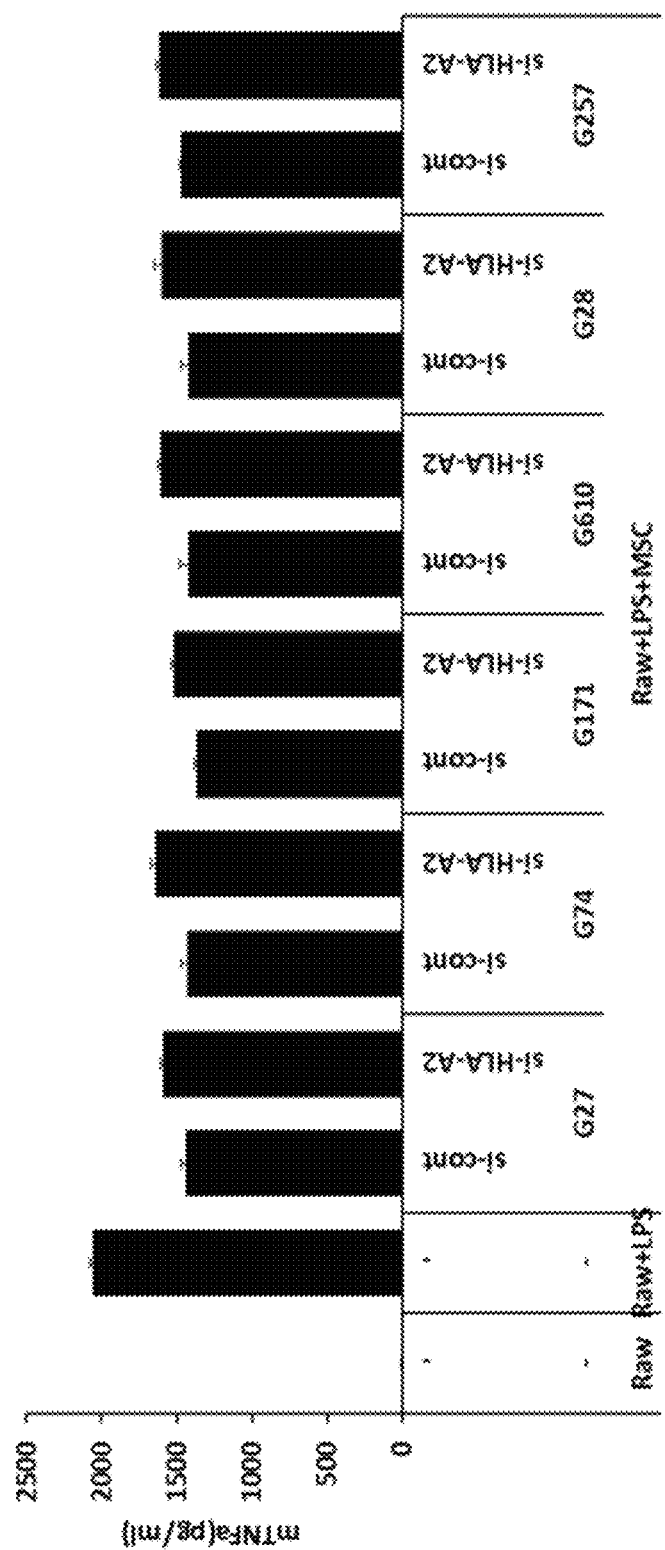
FIG. 3 illustrates results obtained by measuring an amount of mTNF-α secreted in Raw264.7 cells, in which an inflammatory response had been induced, in a case where the Raw264.7 cells were co-cultured with mesenchymal stem cells expressing HLA-A2 which had been treated with control siRNA (HLA-A2(+)-MSC-siCON) or siRNA against HLA-A2 (HLA-A2(+)-MSC-siHLA-A2).

As a result, in a case where the mesenchymal stem cells expressing HLA-A2 were treated with the control siRNA (HLA-A2(+)-MSC-siCON), an amount of secreted TNF-α decreased. On the other hand, in a case where the mesenchymal stem cells expressing HLA-A2 were treated with the siRNA against HLA-A2 (HLA-A2(+)-MSC-siHLA-A2), an amount of secreted TNF-α did not significantly decrease (FIG. 3).

Figure 4:
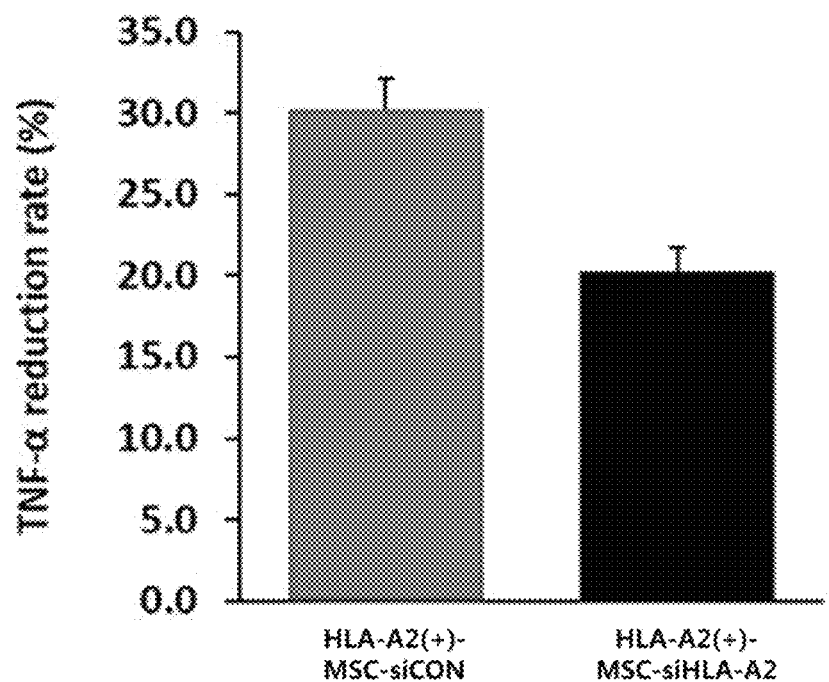
FIG. 4 illustrates results obtained by calculating a mTNF-α secretion reduction rate in Raw264.7 cells, in which an inflammatory response had been induced, in a case where the Raw264.7 cells were co-cultured with mesenchymal stem cells expressing HLA-A2 which had been treated with control siRNA (HLA-A2(+)-MSC-siCON) or siRNA against HLA-A2 (HLA-A2(+)-MSC-siHLA-A2).

In addition, a comparison was made in terms of TNF-α secretion reduction rate between a case where the mesenchymal stem cells expressing HLA-A2 were treated with the control siRNA (HLA-A2(+)-MSC-siCON) and a case where the mesenchymal stem cells expressing HLA-A2 were treated with the siRNA against HLA-A2 (HLA-A2(+)-MSC-siHLA-A2). As a result, the TNF-α secretion reduction rate decreased in the case where the mesenchymal stem cells expressing HLA-A2 were treated with the siRNA against HLA-A2, which identified that inhibition of expression of HLA-A2 in mesenchymal stem cells also resulted in decreased inflammation inhibitory effect of the mesenchymal stem cells (FIG. 4).

Example 4: Identification of Changes in Expression Level of HLA-A2 in Mesenchymal Stem Cells Depending on Number of Passages Thereof To identify whether expression of HLA-A2 in umbilical cord blood-derived mesenchymal stem cells changes depending on the number of passages thereof, mesenchymal stem cells were initially isolated from umbilical cord blood, and then an HLA-A2 expression pattern was analyzed using the mesenchymal stem cells (passage 2, P2, G028), which had been passaged 2 times, and the mesenchymal stem cells (passage 6, P6, G171), which had been passaged 6 times.

Figure 5:
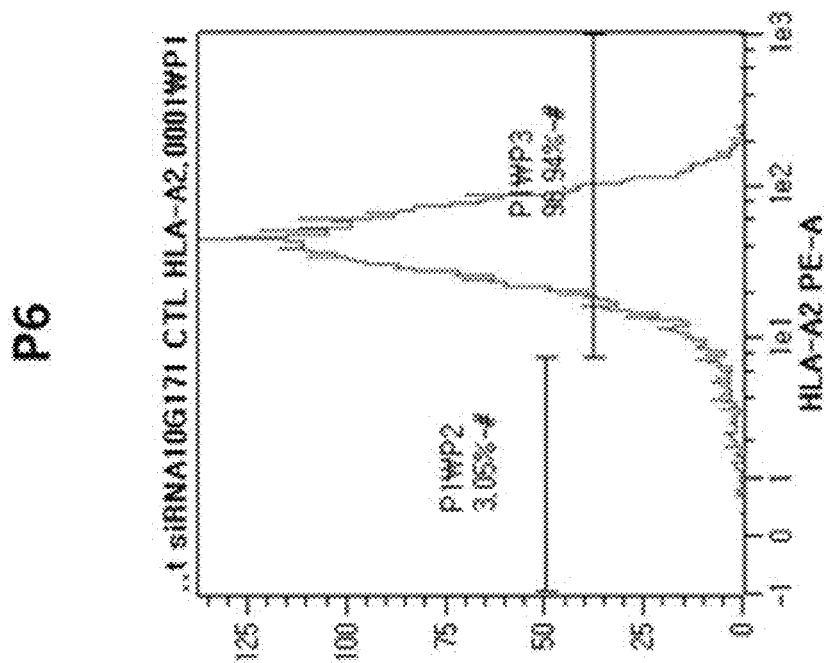
FIG. 5 illustrates results obtained by analyzing an HLA-A2 expression pattern in mesenchymal stem cells (P2) which were passaged 2 times, and mesenchymal stem cells (P6) which were passaged 6 times.
Figure 5:
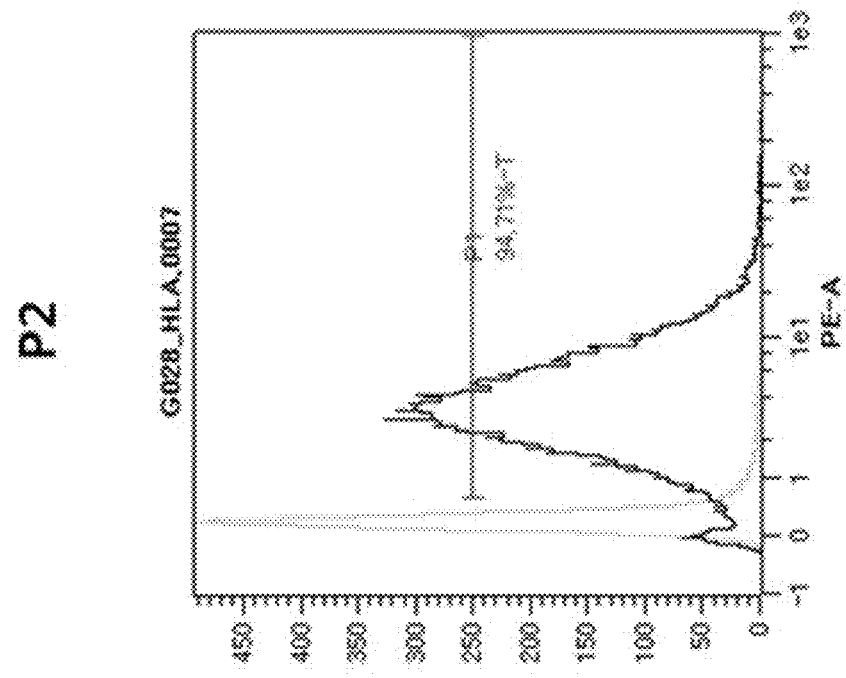

FACS analysis was performed with anti-HLA-A2 antibody in the same manner as in Example 1. As a result, all of the mesenchymal stem cells which had been passaged 2 times and 6 times, respectively, expressed HLA-A2 at a level of 90% or higher, which identified that the mesenchymal stem cells expressed HLA-A2 regardless of the number of passages (FIG. 5).

Example 5: Identification of Therapeutic Effect of Umbilical Cord Blood-Derived Mesenchymal Stem Cells Expressing HLA-A2 on Surface Thereof Using Bronchopulmonary Dysplasia Mouse Model Bronchopulmonary dysplasia is a disease characterized by abnormalities in lung structure and arrested lung development. This is one of inflammatory diseases in which pulmonary inflammation is excessively induced to result in lung damage in a process of applying, to newborns with respiratory distress, high-concentration oxygen therapy through an oxygen ventilator. To date, there are no fundamental treatments and treatment methods for bronchopulmonary dysplasia worldwide.

Therefore, it was identified whether therapeutic effects such as regeneration of immature lung tissue and inhibition of inflammation were observed in a case where umbilical cord blood-derived mesenchymal stem cells expressing HLA-A2 on a surface thereof were administered to a bronchopulmonary dysplasia mouse model.

Specifically, to reflect a condition of high oxygen concentration caused by therapy through an oxygen ventilator after birth, pregnant mother mice were obtained and allowed to give birth. Then, newborn mice within 10 hours of birth were moved to a cage with normal or high oxygen concentration, and reared. Each of the mother mice that gave birth was also moved to the same cage for rearing the newborn mice, and reared. Here, from the viewpoints that fluctuations in the number of newborn mice to be given birth from pregnant mother mice may occur, and an average mortality rate is about 50% in a case where newborn mice are reared at a condition of high oxygen concentration, a total of 18 mice were reared in each group so that the number of the final mice was 9 in each group. Out of the 9 mice, 3 mice were used for morphological analysis of lung tissues, 3 mice were used for alveolar solution extraction to identify inflammatory substances, and the remaining 3 mice were used for RNA or protein analysis. Description of each group is shown in Table 2 below.

TABLE 2

| Description of group | Number of individuals (n) |
| --- | --- |
| Group under normal oxygen concentration (Normal) | 18 |
| Group under high oxygen concentration, administered PBS (Hyperoxia-PBS) | 18 |
| Group under high oxygen concentration, administered HLA-A2(+) mesenchymal stem cells (Hyperoxia-HLA-A2(+)-MSC) | 18 |
| Group under high oxygen concentration, administered HLA-A2(+) mesenchymal stem cells treated with control siRNA (Hyperoxia-HLA-A2(+)-MSC-siCON) | 18 |
| Group under high oxygen concentration, administered HLA-A2(+) mesenchymal stem cells treated with siRNA against HLA-A2 (Hyperoxia-HLA-A2(+)-MSC-siHLA-A2) | 18 |

On day 3 of birth, the newborn mice were intraperitoneally injected with 50 mg/ml of ZOLETIL™ 50 and 23.32 mg/ml of ROMPUN™ as anesthetic agents. Then, PBS, mesenchymal stem cells expressing HLA-A2 (HLA-A2(+)), or mesenchymal stem cells treated with control siRNA (siCON) or siRNA against HLA-A2 (siHLA-A2) were administered into the airway of the newborn mice. Here, for the group administered the mesenchymal stem cells, $5\times10^5$ mesenchymal stem cells per newborn mouse were suspended in 50 µl of PBS and administered once. Then, on day 14 of birth, the anesthetic agents were again injected intraperitoneally into the mice. Lung tissues were harvested and analyzed. Blocks of the lung tissue, which had been fixed in 4% formaldehyde for 24 hours, were embedded in paraffin, cut to 4-µm thick sections, stained histologically with hematoxylin/eosin, and observed histologically with an optical microscope. In this manner, a therapeutic effect of the mesenchymal stem cells expressing HLA-A2 on the lung tissue, for which damage had been induced by high oxygen concentration, was evaluated by comparison.

Figure 6:
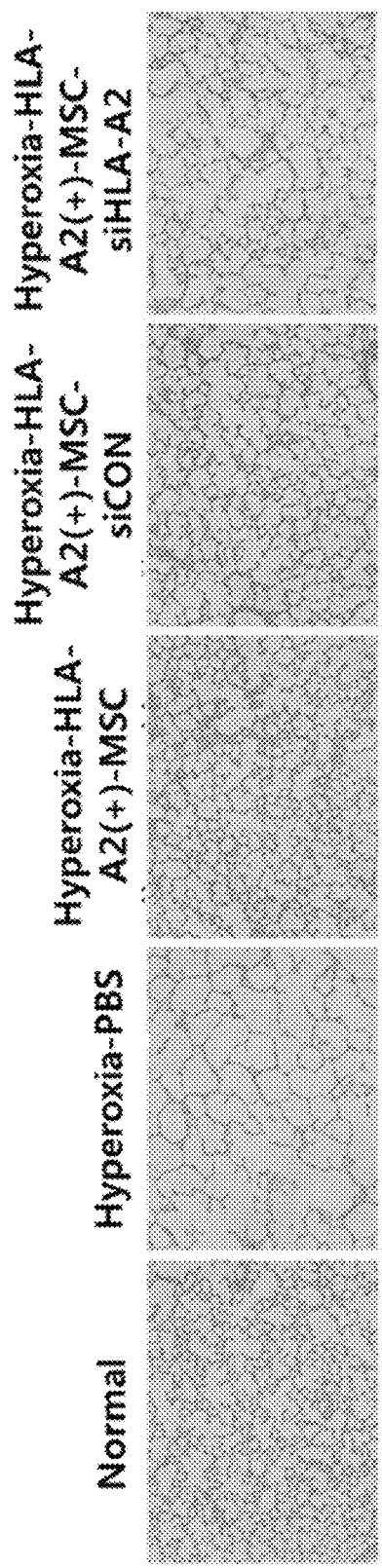
FIG. 6 illustrates photographs obtained by administering, to a bronchopulmonary dysplasia mouse model, PBS, mesenchymal stem cells expressing HLA-A2 (HLA-A2(+)-MSC), or mesenchymal stem cells treated with control siRNA (HLA-A2(+)-MSC-siCON) or siRNA against HLA- A2 (HLA-A2(+)-MSC-siHLA-A2), and then staining lung tissues harvested from the mice on day 14.

As a result, the group (Hyperoxia-PBS), which was administered PBS only after damage had been induced by high oxygen concentration, had lung tissues with severe alveolar damage, as compared with lung tissues of the group under normal oxygen concentration. For this alveolar damage, the group administered the mesenchymal stem cells expressing HLA-A2 or the administration group (Hyperoxia-HLA-A2(+)-MSC-siCON), of the present invention, had an alveolar protective or therapeutic effect similar to that in the group under normal oxygen concentration. On the other hand, little therapeutic effect was observed in the administration group (Hyperoxia-HLA-A2(+)-MSC-siHLA-A2). From these results, it was identified that the umbilical cord blood-derived mesenchymal stem cells expressing HLA-A2 could treat pulmonary inflammation and lung damage which had been caused by high oxygen concentration (FIG. 6).

Figure 7:
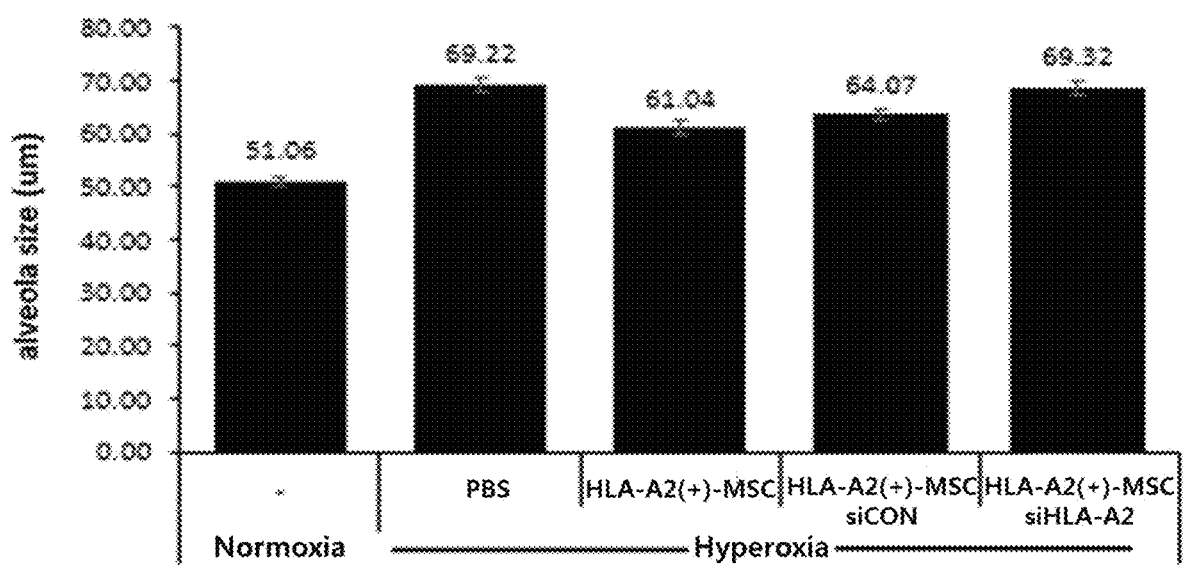
FIG. 7 illustrates results obtained by administering, to a bronchopulmonary dysplasia mouse model, PBS, mesenchymal stem cells expressing HLA-A2 (HLA-A2(+)-MSC), or mesenchymal stem cells treated with control siRNA (HLA-A2(+)-MSC-siCON) or siRNA against HLA-A2 (HLA-A2(+)-MSC-siHLA-A2), and then measuring alveolar size in lung tissues harvested from the mice on day 14.

In addition, a degree of alveolar damage was quantified as a mean linear index. As a result, as illustrated in FIG. 7, the bronchopulmonary dysplasia model group (Hyperoxia-PBS) had a significantly high mean linear index due to impaired alveolar development as compared with the normal group. It can be seen that the group administered the mesenchymal stem cells expressing HLA-A2 or the administration group (Hyperoxia-HLA-A2(+)-MSC-siCON) had a significantly lowered mean linear index due to improved lung damage. On the other hand, the administration group (Hyperoxia- HLA-A2(+)-MSC-siHLA-A2) did not have a significantly lowered mean linear index due to little therapeutic effect (FIG. 7).

Example 6: Identification of Therapeutic Effect of Umbilical Cord Blood-Derived Mesenchymal Stem Cells Expressing HLA-A2 on Surface Thereof Using Alzheimer's Disease Mouse Model As an Alzheimer's disease mouse model, 6-month-old 5XFAD mice (Jackson Laboratory, USA) were used. In the 5XFAD mice, amyloid-beta begins to be produced in brain tissue from 2 months of age; amyloid-beta accumulates in brain tissue at 4 months of age; and cognitive impairment appears around 6 months of age. The 6-month-old 5XFAD mice were intraperitoneally administered 5 μl of anesthetic agent per mouse body weight (g), in which the anesthetic agent used was a mixture of ZOLETIL™, ROMPUN™, and physiological saline at a ratio of 4:1:5.

For intraventricular administration of the mesenchymal stem cells expressing HLA-A2 isolated in Example 1, a guide cannula was inserted in a target location (from bregma, anterior/posterior: −0.22 mm, medial/lateral: 1.0 mm, dorsal/ventral: 2.5 mm), and then fixed with screws placed around the cannula. Then, the mice were given a recovery period of 6 to 8 days for recovery. Then, the umbilical cord blood-derived mesenchymal stem cells expressing HLA-A2 were transferred to a Hamilton syringe, and then an internal cannula thereof was placed in the guide cannula. Intraventricular injection was performed at an infusion rate of 0.5 μl/min. Here, description of each group is shown in Table 3 below.

TABLE 3

| Group | | Time of sacrifice after initial administration | | Number of animals |
|---|---|---|---|---|
| | | Week 12 (Test A) | Week 20 (Test B) | |
| Control* (15 μl of 5% MEM-alpha and 95% saline) | | 8 (M) | 8 (M) | 16 (M) |
| HLA-A2(+) MSC (1 × 10⁵ cells/15 μl) | Administered once (Single) | 8 (M) | — | 8 (M) |
| | Administered repeatedly (Repeat) (3 times) | 8 (M) | 8 (M) | 16 (M) |
| Total number of animals (M = male 5XFAD) | | | | 40 (M) |

At the time of sacrifice, an appropriate amount of anesthetic agent was administered intraperitoneally depending on body weight, and then cardiac perfusion was performed using a peristaltic pump. First, to expose the heart, the skin, diaphragm, and ribs of the mice were cut, and pump tubing was connected to the left ventricle. Then, PBS was circulated in the body to discharge blood.

Thereafter, brain tissue was collected and stored frozen at −80° C. The brain tissue was lysed using a lysis buffer and a sonicator. Then, using a Bradford assay, the brain tissue lysate was diluted and used. Cytokine ELISA KITs, suitable for measuring lysates such as those of brain tissue, were used. Proinflammatory cytokines were analyzed using TNF-α ELISA KIT (PeproTech, 900K54EK™) and IFN-γ ELISA KIT (RayBio, ELM-IFNg-CL™); and anti-inflammatory cytokines were analyzed using CD163 ELISA KIT (LSBio, Cat No. LS-F9079) and Arg-1 ELISA KIT (LSBio, Cat No. LS-F6864).

Figure 8:
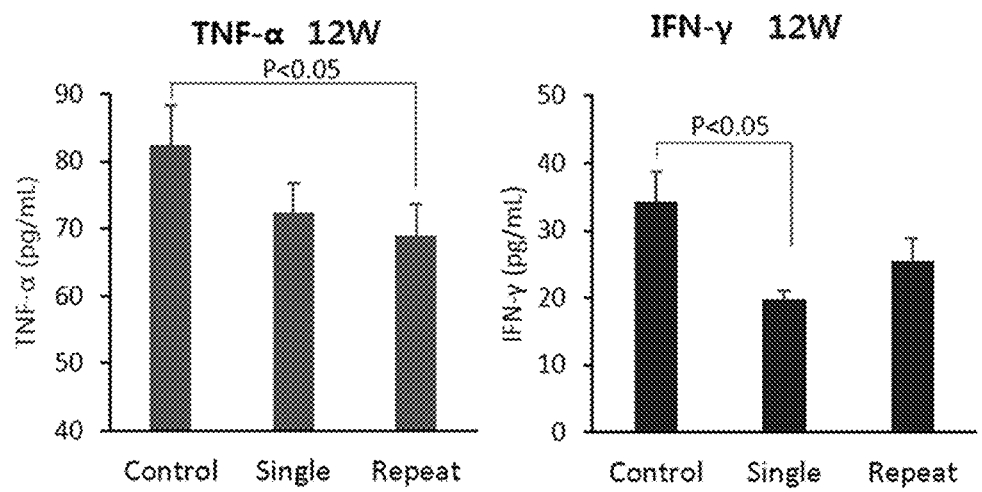
FIG. 8 illustrates results obtained by administering, to an Alzheimer's disease mouse model, physiological saline (Control) or mesenchymal stem cells expressing HLA-A2, in which the mesenchymal stem cells were administered once (Single) or repeatedly (Repeat), and then identifying expression levels of TNF-α and IFN-γ in brain tissues harvested from the mice on week 12.
Figure 9:
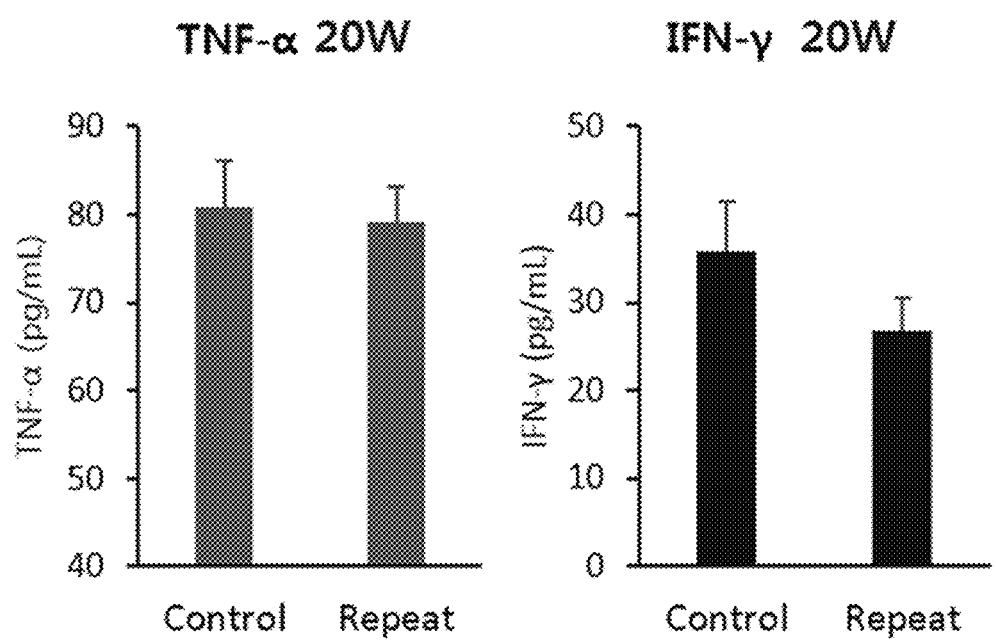
FIG. 9 illustrates results obtained by administering, to an Alzheimer's disease mouse model, physiological saline (Control) or mesenchymal stem cells expressing HLA-A2, in which the mesenchymal stem cells were administered once (Single) or repeatedly (Repeat), and then identifying expression levels of TNF-α and IFN-γ in brain tissues harvested from the mice on week 20.

As a result, as compared with the control, TNF-α and INF-γ decreased under both conditions of Test A (week 12) and Test B (week 20) in the experimental group in which the mesenchymal stem cells expressing HLA-A2 were administered once and the experimental group in which the mesenchymal stem cells expressing HLA-A2 were administered repeatedly. In particular, as compared with the control, TNF-α decreased in a statistically significant manner in the experimental group in which the mesenchymal stem cells expressing HLA-A2 were administered repeatedly, and INF-γ decreased in a statistically significant manner in the experimental group in which the mesenchymal stem cells expressing HLA-A2 were administered once (FIGS. 8 and 9). From these results, it was identified that anti-inflammatory efficacy was maintained even after time elapsed in a case where the mesenchymal stem cells were administered repeatedly.

Figure 10:
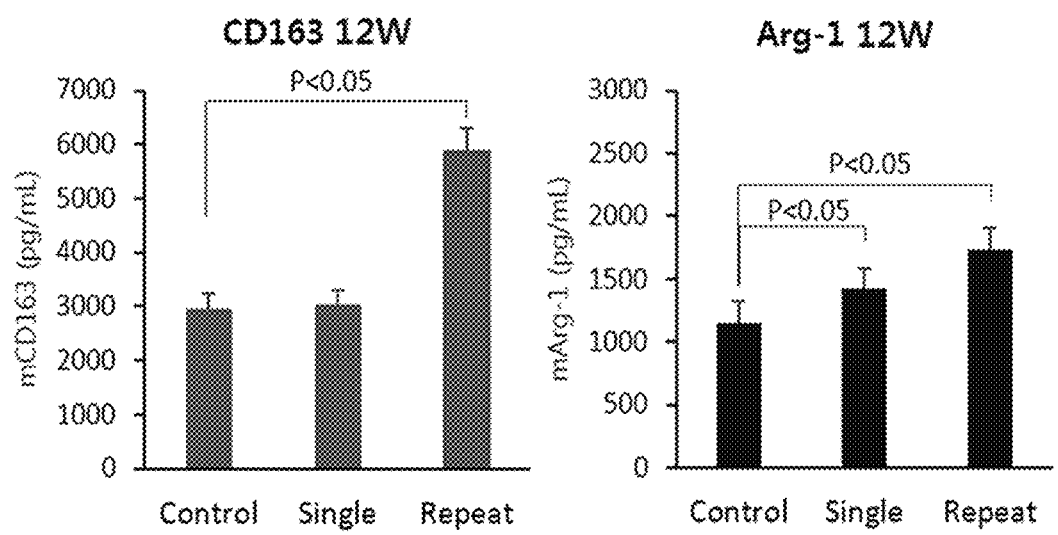
FIG. 10 illustrates results obtained by administering, to an Alzheimer's disease mouse model, physiological saline (Control) or mesenchymal stem cells expressing HLA-A2, in which the mesenchymal stem cells were administered once (Single) or repeatedly (Repeat), and then identifying expression levels of CD163 and Arg-1 in brain tissues harvested from the mice on week 12.
Figure 11:
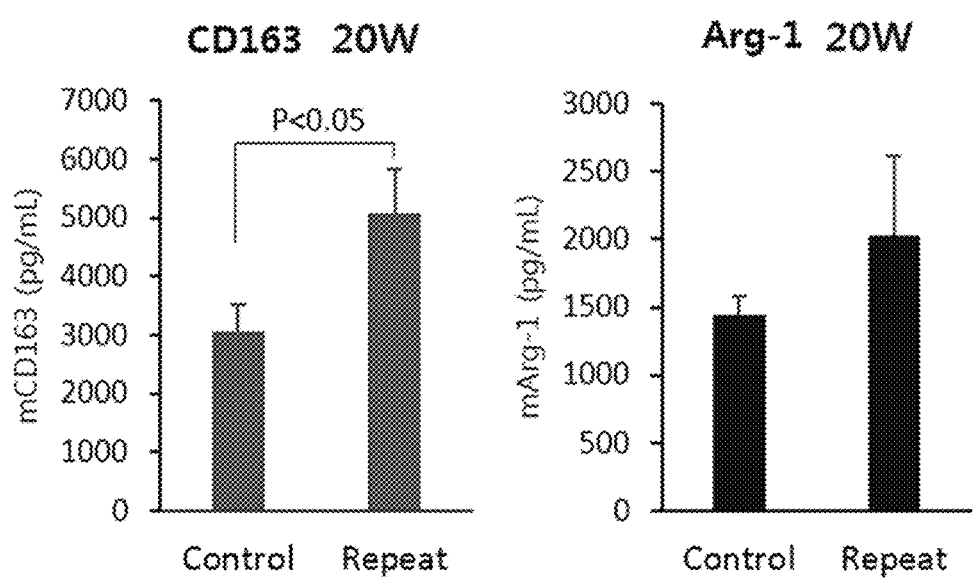
FIG. 11 illustrates results obtained by administering, to an Alzheimer's disease mouse model, physiological saline (Control) or mesenchymal stem cells expressing HLA-A2, in which the mesenchymal stem cells were administered once (Single) or repeatedly (Repeat), and then identifying expression levels of CD163 and Arg-1 in brain tissues harvested from the mice on week 20.

In addition, CD163 and arginase-1 (Arg-1), which were typically known as anti-inflammatory cytokines in brain tissue, were analyzed by ELISA. As a result, as compared with the control, CD163 and Arg-1 increased under both conditions of Test A (week 12) and Test B (week 20) in the experimental group in which the mesenchymal stem cells expressing HLA-A2 were administered once and the experimental group in which the mesenchymal stem cells expressing HLA-A2 were administered repeatedly. In particular, as compared with the control, CD163 increased in a statistically significant manner in the experimental group in which the mesenchymal stem cells expressing HLA-A2 were administered repeatedly, and Arg-1 increased in a statistically significant manner in both the experimental group in which the mesenchymal stem cells expressing HLA-A2 were administered once and the experimental group in which the mesenchymal stem cells expressing HLA-A2 were administered repeatedly (FIGS. 10 and 11). From these results, it was identified that anti-inflammatory efficacy was maintained even after time elapsed in a case where the mesenchymal stem cells were administered repeatedly.

The invention claimed is:

1. A method for treating an inflammatory disease in a subject in need thereof, comprising,
analyzing the presence of a cell surface antigen on the surface of a population of mesenchymal stem cells, said cell surface antigen comprising HLA-A2;
determining whether 70% or more mesenchymal stem cells of the population express HLA-A2 on a surface thereof to select a population of mesenchymal stem cells of which 70% or more mesenchymal stem cells express HLA-A2; and
administering to the subject a pharmaceutical composition comprising the selected population of mesenchymal stem cells of which 70% or more mesenchymal stem cells expressing HLA-A2, thereby treating said inflammatory disease,
wherein the administration of mesenchymal stem cells increases the expression of CD163 and Arg-1 in the subject, compared to a control subject to which a physiological saline without the mesenchymal stem cells is administered,
wherein the mesenchymal stem cells are derived from umbilical cord blood, and
wherein the 70% or more mesenchymal stem cells of the population express, on the surface thereof, each of CD73, CD90, CD105, and CD166.

2. The method of claim 1, wherein the mesenchymal stem cells expressing HLA-A2 substantially do not express any one selected from the group consisting of CD14, CD34, CD45, and HLA-DR.

3. The method of claim 2, wherein 1% or less mesenchymal stem cells of the population express each of CD14, CD34, CD45, and HLA-DR.

4. The method of claim 1, wherein the population of mesenchymal stem cells meet that:
75% or more mesenchymal stem cells of the population express, on the surface thereof, HLA-A2, and
1% or less mesenchymal stem cells of the population express each of CD14, CD34, CD45, and HLA-DR.

5. The method of claim 1, wherein the inflammatory disease is rheumatoid arthritis, atopy, asthma, allergic rhinitis, Alzheimer's disease, graft versus host disease (GVHD), diabetic nephropathy, Crohn's disease, inflammatory bowel disease, rejection after transplantation, bronchopulmonary dysplasia (BPD), or chronic obstructive pulmonary disease (COPD).

6. The method of claim 2, wherein the inflammatory disease is rheumatoid arthritis, atopy, asthma, allergic rhinitis, Alzheimer's disease, graft versus host disease (GVHD), diabetic nephropathy, Crohn's disease, inflammatory bowel disease, rejection after transplantation, bronchopulmonary dysplasia (BPD), or chronic obstructive pulmonary disease (COPD).

7. The method of claim 3, wherein the inflammatory disease is rheumatoid arthritis, atopy, asthma, allergic rhinitis, Alzheimer's disease, graft versus host disease (GVHD), diabetic nephropathy, Crohn's disease, inflammatory bowel disease, rejection after transplantation, bronchopulmonary dysplasia (BPD), or chronic obstructive pulmonary disease (COPD).

8. The method of claim 4, wherein the inflammatory disease is rheumatoid arthritis, atopy, asthma, allergic rhinitis, Alzheimer's disease, graft versus host disease (GVHD), diabetic nephropathy, Crohn's disease, inflammatory bowel disease, rejection after transplantation, bronchopulmonary dysplasia (BPD), or chronic obstructive pulmonary disease (COPD).

* * * * *